United States Patent [19]

Burton et al.

[11] 4,196,121

[45] Apr. 1, 1980

[54] BLOCKING PROTEIN FRACTIONS, RECOVERY METHODS AND PRODUCTS

[75] Inventors: Lawrence Burton, Commack; Frank Friedman, New York, both of N.Y.

[73] Assignee: Immunology Research Foundation, Inc., Great Neck, N.Y.

[21] Appl. No.: 880,547

[22] Filed: Feb. 23, 1978

Related U.S. Application Data

[63] Continuation-in-part of Ser. No. 600,028, Jul. 29, 1975, Pat. No. 4,082,733.

[51] Int. Cl.$^2$ .................................................. A23J 1/06
[52] U.S. Cl. ...................... 260/112 B; 210/DIG. 23; 435/2
[58] Field of Search .................. 260/112 R, 112 B; 23/258.5 R; 210/DIG. 23

*Primary Examiner*—Paul R. Michl
*Attorney, Agent, or Firm*—Barry Kramer

[57] ABSTRACT

A process is provided for the isolation of two protein fractions herein termed the "blocking protein fractions" or "Blocker I" and "Blocker II," from mammalian blood. The process comprises a series of centrifugal separations of blood fractions under conditions which maintain the integrity of the desired material as it existed in vivo. These blocking protein fractions are new materials and they constitute another aspect of the invention. Isolated Blocker I and Blocker II, which are natural proteins or derivatives thereof, are useful to prevent tissue implant rejection, and as standards for the determination of the tumor remission activity of other materials isolated from blood.

6 Claims, No Drawings

BLOCKING PROTEIN FRACTIONS, RECOVERY METHODS AND PRODUCTS

CROSS-REFERENCE TO RELATED APPLICATION

This is a continuation-in-part of our copending application Ser. No. 600,028 filed on July 29, 1975, now U.S. Pat. No. 4,082,733.

FIELD OF THE INVENTION AND PRIOR PUBLICATIONS

The present invention relates to a method for isolating specific fractions of mammalian blood. It relates further to the provision of a composition which can be administered to prevent tissue implant rejection. It relates still further to the use of said fractions to determine the tumor remission activity of other substances isolated from blood.

The inventors have published the following articles, relating to the field of this invention:
1. Annals of The New York Academy of Sciences, Vol. 100, Part II, pages 791-814 (1963)
2. Pigment Cell Biology, pages 279-299, Academic Press, 1959
3. Transactions of The New York Academy of Sciences, Ser. II, Vol. 25, pages 29-32 (Nov. 1962)

BACKGROUND OF THE INVENTION

In application Ser. No. 600,028 referred to above and in related applications filed concurrently therewith, we disclosed several inventions relating to tumor remission and prevention in mammals. One aspect of these inventions is the detection, remission and prevention of tumors. These inventions arose, in part, as a result of the assumption that the body has within it an anti-cancer immune defense mechanism which prevents or controls the formation of tumor cells, and that tumors arise only when this system does not function properly or sufficiently, either due to an imbalance which may be genetic in origin, or the presence of more cancer producing stress than the mammal's system can handle.

Based upon the foregoing, we proceeded to fractionate mammalian blood. Since the materials sought were unknown in structure, the properties vis-á-vis their effect on the mammal, had to be determined empirically. For example, if a fraction of the mammal's blood is injected into a tumor bearing mouse and the tumor does not respond, then the blood may be centrifuged to give a sediment and a supernatant, each of which is again tested on the mice. If again the tumors do not respond, then perhaps the blood fraction is centrifuged at a higher speed and the resultant materials are again tested. If it turns out that the resultant sediment causes a positive anti-tumor response, then it is clear that centrifuging at the higher speed resulted in the separation of a tumor-controlling component. Also considered was the presence of a material in the supernatant which, before being separated from the active sediment, inhibited the tumor activity of the material in the sediment.

Proceeding in the foregoing fashion, the Applicants were able to isolate three blood components or fractions, the presence in balanced proportion of which, both inhibit the formation and cause necrosis of neoplasmic tissue. These components are virtually non-toxic and have no apparent side effects or adverse effect on normal tissue. The toxicity is so minimal that an $LD_{50}$ has thus far not been obtainable.

Although the chemical structure of these components has not been illucidated, the materials have been identified and named as follows:
1. Tumor Complement Fraction ("TCF") a peptide chain or derivative thereof that attacks the tumor and causes necrosis of the tumor tissue. Process for isolation is disclosed in co-pending Application Ser. No. 600,027, filed on July 29, 1975.
2. Blocking Protein Fraction ("BPF") a substance that blocks the activity of TCF. Process for isolation is disclosed in Application Ser. No. 600,028 set forth above.
3. De-Blocking Protein Fraction ("DPF") a protein or derivative thereof that neutralizes or "deblocks" BPF. Process for isolation is disclosed in co-pending Application Ser. No. 600,026, filed July 29, 1975.

TCF, BPF, and DPF must be in balance to maintain a tumor free condition. In a normal animal, tumor growth is prevented by the presence of a greater amount of TCF than BPF, there being generally seven units of TCF for each unit of BPF. In a tumor-bearing animal, less TCF is present in the blood. By administering DPF to a tumor-bearing animal, it is theorized that TCF which is bound to be BPF, can be freed again to do its work of killing tumor cells. If TCF is added along with DPF, the necrosis of tumor tissue can be made to proceed at a more rapid rate. Thus, the essence of tumor treatment according to the principles stated in the above-referred to applications, is to administer TCF and/or DPF to thereby provide free TCF capable of necrosizing the tumorous tissue.

As a collorary to the foregoing conclusions, it was concluded that BPF has an inactivating effect on the body's immune defense system and can be used to prevent tissue implant rejection and it has been found that this is the case.

It has now been discovered that there exists another blocking protein fraction, having much the same activity as the BPF disclosed in the aforementioned Applications Ser. No. 600,026, 600,027 and 600,028. Said BPF is now termed "Blocker I". The newly discovered blocking protein fraction will here be termed "Blocker II".

With Blocker I and Blocker II, we are provided with useful methods to assay the activity of TCF and DPF which, as disclosed in the aforementioned copending applications, are useful in effecting necrosis of tumor tissue.

Accordingly, it is one object of the present invention to provide a method of extracting Blocker I and Blocker II from mammalian blood without significantly altering or modifying the materials from their in vivo condition.

It is a further object of the present invention to provide mammalian blood components which tend to inactivate the body's immune defense system thereby reducing the tendency of the body to reject tissue implants.

It is a still further object of the present invention to provide material which can be used to assay the antitumor activity of TCF and DPF.

SUMMARY OF THE INVENTION

The following Table shows the steps which can be employed to isolate Blocker I and Blocker II from mammalian blood.

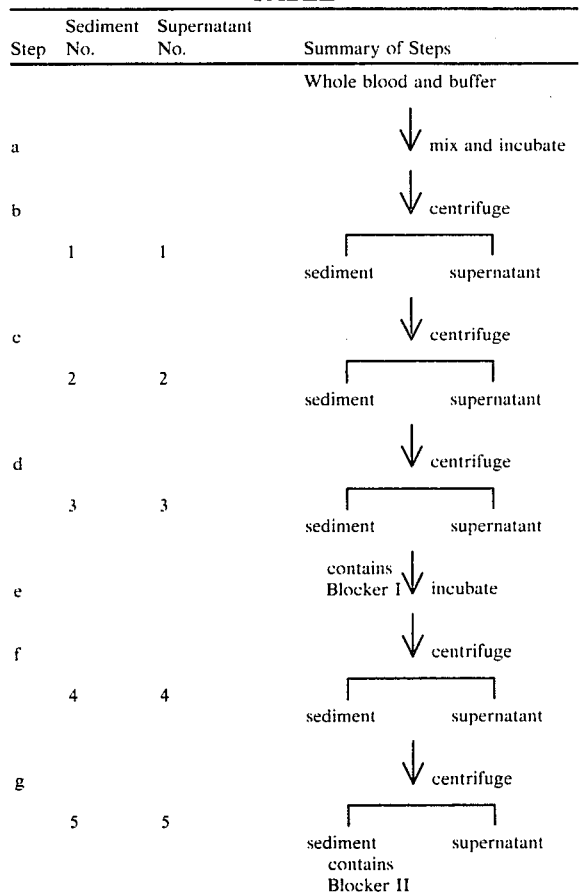

TABLE

| Step | Sediment No. | Supernatant No. | Summary of Steps |
|---|---|---|---|
| | | | Whole blood and buffer |
| a | | | mix and incubate |
| b | | | centrifuge |
| | 1 | 1 | sediment / supernatant |
| c | | | centrifuge |
| | 2 | 2 | sediment / supernatant |
| d | | | centrifuge |
| | 3 | 3 | sediment / supernatant |
| e | | | contains Blocker I / incubate |
| f | | | centrifuge |
| | 4 | 4 | sediment / supernatant |
| g | | | centrifuge |
| | 5 | 5 | sediment contains Blocker II / supernatant |

DETAILED DISCLOSURE

Blocker I and Blocker II are obtained by fractionating mammalian whole blood. In Step (a), a sample of whole blood is thoroughly mixed with a buffer solution at near neutral pH such as $KH_2PO_4$ (0.5 M) titrated to pH 7.5 with $Na_2HPO_4$ (0.05 M) at 42° C. and incubated at said temperature for 4 minutes. The amount of buffer relative to whole blood is not critical, but preferably 0.1 ml of whole blood is admixed with 2.0 ml of buffer.

In Step (b), the buffer solution is centrifuged at 5400 to 10,000 g, preferably 6500 g, for several minutes (e.g., five minutes) to obtain Sediment 1 (which is discarded) and Supernatant 1.

In Step (c), Supernatant 1 is again centrifuged under the same conditions. Sediment 2 is discarded and Supernatant 2 is again centrifuged (Step (d)) but this time at between 20,000 and 25,000 g, preferably 23,500 g for about 15 minutes. The resultant Sediment 3 contains Blocker I and it may be resuspended with 1.5 ml of an alkaline buffer such as $Na_2HPO_4$ (0.05 M, pH 9.2).

The Blocker I obtained above can be further purified, if desired, by heating the solution to at least 55° C. for about ten minutes and then centrifuging at between about 20,000 and 25,000 g (preferably 23,500 g) for about 15 minutes. The resultant supernatant is believed to be pure Blocker I.

Supernatant 3 is incubated at 55° C. for about ten minutes (Step (e)) and then centrifuged at between about 7,000 and 12,000 g, preferably 10,000 g for about ten minutes, to obtain Sediment 4 and Supernatant 4. Sediment 4 is discarded.

In Step (g), Supernatant 4 is further centrifuged at between about 20,000 and 25,000 g, preferably 23,500 g, for about ten minutes. The resultant Sediment 5 contains Blocker II, which may be resuspended and purified in like manner as Blocker I. Supernatant 5 is discarded.

To determine the concentration of Blocker I and Blocker II isolated from 0.1 ml of whole blood, the resultant respective supernatant fluids are analyzed in a Beckman ACTA V spectrophotometer. Since neither Blocker I nor Blocker II has a peak absorption at a wave length in the far U.V. range that is within the capability of this model spectrophotometer, measurements of sample "cut-off" were used as quantitative indicators. Usually the term "cut-off" is used in reference to a solvent, but it can be applied to everything that has a wave length of maximum absorption near or below the instruments lower wave length limit. The strict definition of "cut-off" is the wave length at which the absorbance in a one centimeter cell is equal to 1.0. For measurement of Blocker I and Blocker II, a 0.5 centimeter cell is used in order to perform more effectively with minimal volumes at the lower wave length and to determine the wave length at which the absorbance is 0.5. When the read-out display of the Beckmann ACTA V for any sample indicates 0.5 absorbance, the wave length is referred to Blocker assay curves. These curves are constructed experimentally by serial dilutions of more than 400 samples each of Blocker I and Blocker II. In these linear assay curves, starting at 197 nm, each 1.0 nm increase is equivalent to an increment of 3.2 units of Blocker I or Blocker II.

Preliminary investigations have indicated that Blocker I and Blocker II are peptides. Analysis of material isolated from large batches of blood (200—200 milliliters) indicated that they are proteinaceous.

Blocker I and Blocker II have utility as standards against which activity of TCF and DPF can be measured. The means for using both of these blocking agents are disclosed in the aforementioned copending applications in terms of "BPF", pertinent portions of which are herein incorporated by reference. In assays of blood taken from animals suffering from tumor conditions and currently under treatment with TCF and/or DPF, Blocker I appears to be present in blood serum as the result of recent tumor cell death (0 to 48 hours), while Blocker II appears to be present in serum as the result of "old" tumor cell death (7 to 14 days). Thus, the assay of Blocker I and II can be useful in determining the efficacy of treatment with other blood fractions.

These blocking protein fractions are also useful to prevent rejection of tissue implants. subcutaneous or intramuscular administration of Blocker I or Blocker II tends to prevent the rejection of implanted tissue as the result of the body's IDMC. The amount of blocking protein fraction to be administered depends upon the amount of unassociated blocking protein fraction in the subject's blood. This can be determined by the assay methods disclosed in the aforementioned copending applications. Usually the amount of Blocker I and/or Blocker II to be administered should be such that, after administration, the total amount of blocking protein fraction in the blood exceeds one unit for each seven units of TCF in the blood.

What is claimed is:

1. A process for the isolation of Blocker II which comprises:
   (a) suspending whole blood in a buffer solution of nearly neutral pH;
   (b) centrifuging the whole blood suspension at 5400 to 10,000 g to obtain a first supernatant;
   (c) centrifuging the first supernatant at 5400 to 10,000 g to give a second supernatant;
   (d) centrifuging the second supernatant at 20,000 to 25,000 g to give a third supernatant;
   (e) incubating the third supernatant at a temperature of 55° C.;
   (f) centrifuging the third supernatant at 7,000–12,000 g to obtain a fourth supernatant;
   (g) centrifuging the fourth supernatant at 20,000–25,000 g to give a Blocker II sediment; and
   (h) optionally, purifying the Blocker II sediment by resuspending in an alkaline buffer and centrifuging at 20,000–25,000 g to give a supernatant containing essentially pure Blocker II.

2. The process of claim 1 wherein the centrifuging of Step (f) is conducted at 10,000 g.

3. The process of claim 1 wherein the centrifuging of Step (g) is conducted at 23,500 g.

4. A process for the isolation of Blocker II comprising:
   (a) suspending whole blood in a buffer solution of nearly neutral pH;
   (b) centrifuging the whole blood suspension at 6500 g to obtain a first supernatant;
   (c) centrifuging the first supernatant at 6500 g to obtain a second supernatant;
   (d) centrifuging the second supernatant at 23,500 g to obtain a third supernatant;
   (e) incubating the third supernatant at a temperature of 55° C.;
   (f) centrifuging the third supernatant at 10,000 g to give a fourth supernatant;
   (g) centrifuging the fourth supernatant at 23,500 g to give a Blocker II sediment; and
   (h) optionally, resuspending said Blocker II sediment in an alkaline buffer and centrifuging at 23,500 g to tive a supernatant containing relatively pure Blocker II.

5. The product produced by the process of claim 1.

6. The product produced by the process of claim 4.

* * * * *